(12) United States Patent
Chen et al.

(10) Patent No.: US 7,198,369 B2
(45) Date of Patent: Apr. 3, 2007

(54) METHOD AND DEVICE FOR DETECTING/CORRECTING COLOR VISION AND THEIR APPLICATION

(75) Inventors: Xiaoguang Chen, Jilin (CN); Yan Chen, Department of Physical Education, Qianweixiaoqu, Jilin University, Jilin 13022 (CN)

(73) Assignee: Yan Chen, Jilin (CN)

( * ) Notice: Subject to any disclaimer, the term of this patent is extended or adjusted under 35 U.S.C. 154(b) by 549 days.

(21) Appl. No.: 10/451,697

(22) PCT Filed: Dec. 26, 2001

(86) PCT No.: PCT/CN01/01645

§ 371 (c)(1),
(2), (4) Date: Oct. 20, 2003

(87) PCT Pub. No.: WO02/051305

PCT Pub. Date: Jul. 4, 2002

(65) Prior Publication Data

US 2004/0061835 A1    Apr. 1, 2004

(30) Foreign Application Priority Data

Dec. 26, 2000  (CN)  ............................. 00 1 36472

(51) Int. Cl.
*A61B 3/06* (2006.01)
*A61B 3/00* (2006.01)

(52) U.S. Cl. ..................... 351/246; 351/242; 351/239

(58) Field of Classification Search .............. 351/205, 351/233, 239, 242, 246
See application file for complete search history.

(56) References Cited

U.S. PATENT DOCUMENTS 2,453,335 A * 11/1948 Burford ...................... 351/242
2,462,485 A * 2/1949 Freeman .................... 351/242
2,937,567 A * 5/1960 Rand et al. ................. 351/242
4,285,580 A    8/1981 Murr
4,844,607 A * 7/1989 Andera et al. .............. 351/243
5,206,671 A    4/1993 Eydelman et al.
5,589,899 A   12/1996 Maeda et al.
5,856,883 A * 1/1999 Sander ....................... 359/389
6,203,157 B1 * 3/2001 Lee ............................ 351/242

(Continued)

FOREIGN PATENT DOCUMENTS

CN   1062832   7/1992

(Continued)

*Primary Examiner*—Charles A. Marmor, II
*Assistant Examiner*—John R Sanders
(74) *Attorney, Agent, or Firm*—Merchant & Gould P.C.

(57) ABSTRACT

This invention discloses an achromatopsia inspection/correction method, comprising the following steps: displaying a plurality of groups of achromatopsia test charts for the examinee to identify, each group is corresponding to one type of achromatopsia; determining the types of achromatopsia based upon the inspection results; displaying at least one colored color-matching contrast chart, one area of said color-matching chart is in a predetermined color, another area is for the examinee to match colors; taking the color-matching result from the examinee; determining the achromatopsia scales of the examinee by comparing the color-matching results of the examinee with said predetermined three elementary colors; selecting the corresponding achromatopsia correction spectrum curves according to the determined types and scales of achromatopsia. Besides, this invention also discloses an achromatopsia inspection/correction apparatus for realizing this method.

19 Claims, 7 Drawing Sheets

U.S. PATENT DOCUMENTS 6,210,006 B1 * 4/2001 Menozzi .................... 351/242

FOREIGN PATENT DOCUMENTS

| CN | 2130497 | 4/1993 |
|---|---|---|
| CN | 1077873 | 11/1993 |
| CN | 1080835 | 1/1994 |
| WO | WO 00/33728 | 6/2000 |

* cited by examiner

METHOD AND DEVICE FOR DETECTING/CORRECTING COLOR VISION AND THEIR APPLICATION

TECHNICAL FIELD

The present invention relates to a color vision inspection/correction method and apparatus, for inspecting the types and scales of achromatopsia, and their applications in achromatopsia correction.

PRIOR ART

The abnormal color vision, with a proverb of "color blindness", is kind of an inherited physiological limitation. As we know; the human brain identifies colors and generates color vision with the inherent tricolor coordinates, based on the size and directions of the vector quantities of the three elementary colors: red (R), green (G) and blue (B). If aberrance occurs in one of the processes of color vision, the balanced vector quantities of the three elementary colors taken by the brain would be maladjusted. However, the brain would still identify colors with the inherent color definitions, this would certainly lead to abnormal color vision, and lead to achromatopsia (see "*Introduction on the Correction of Color Vision*", written by Chen Xiaoguang, published by Jilin Technology Publishing Company, 1992). One of the causes of abnormal color vision is the hyperfunction of one of the three elementary colors. The summation of the three elementary colors is 1, namely R+G+B=1. This would leads to the hypofunction of the other 2 elementary colors. Achromatopsias for this reason are defined as achromatopsia Type A, achromatopsia Type B and achromatopsia Type C. Another cause of abnormal color vision is the excursion of the maximum spectrum absorbance value by one of the three elementary colors. Achromatopsias for this reason are defined as achromatopsia Type D, achromatopsia Type E and achromatopsia Type F. Besides, there is also a complete achromatopsia type.

Presently, there are at least 6 ways of color vision inspection, in which the method of "color vision (achromatopsia) test chart" is most commonly used. The defect of this method is, it can not quantitatively find out the types and scales of the achromatopsia.

Chinese Patent No. 90200939.7 discloses a computerized inspection apparatus for achromatopsia correction, which installs traditional color vision test charts into computers, color vision inspection is conducted by having the examinee to identify the color vision test charts on the display of the computer. The inspection apparatus makes the color vision inspection very accessible, but there are some defects: during the inspection/correction process using this apparatus, the examinee is requested to make identification by himself as clearly as possible, this may easily lead to counterreactional tendency of the examinee. The result may be hypercorrection, or turning into another type of achromatopsia. Although the achromate may pass the achromatopsia inspection after wearing glasses, but he/she cannot reach the goal of real correction, and he/she is still unable to identify colors as normal people do.

CONTENTS OF INVENTION

The intention of this invention is to provide a color vision inspection/correction method and apparatus. Using this method can overcome the counterreactional tendency of the examinee, precisely determine the types and scales of achromatopsia, so as to avoid hypercorrections.

The achromatopsia inspection/correction method in this invention comprises the following steps; displaying a plurality of groups of achromatopsia test charts for the examinee to identify, each group is corresponding to one type of achromatopsia; determining the types of achromatopsia based upon the inspection results; displaying at least one colored matching contrast charts, one area of the color-matching chart is in a predetermined color, another area is for the examinee to match colors; taking the color-matching result from the examinee; determining the achromatopsia scales of the examinee by comparing the color-matching results of the examinee with said predetermined three elementary colors; selecting the corresponding achromatopsia correction spectrum curves according to the determined types and scales of achromatopsia.

The achromatopsia inspection/correction apparatus in this invention comprises: a displaying means for displaying a plurality of groups of achromatopsia test charts, each group is corresponding to one type of achromatopsia for the examinee to identify, and used for displaying at least one colored color-matching contrast charts, one area of the color-matching chart is in a predetermined color, another area is used for the examinee to match colors; a input means, for taking the color-matching result from the examinee; a means for determining the achromatopsia scales of the examinee by comparing the color-matching results from the examinee with said predetermined three elementary colors; a means for selecting the corresponding achromatopsia correction spectrum curves according to the determined type and scale of achromatopsia.

Thus, according to this invention, the incidental counterreactional tendency and hypercorrection of the examinee under the intervention of the inspector can be avoided by making the examinee to do color matching by himself, and determining the achromatopsia scales according to the color-matching results.

Besides, the achromatopsia inspection/correction method in this invention may also include the following steps: providing an achromatopsia correction lens; making the examinee to identify an achromatopsia test chart through said achromatopsia correction lens; altering the angle of said achromatopsia correction lens until the examinee is able to correctly identify said achromatopsia test chart; determining the achromatopsia scales according to said angle. Thus, by using the method of this invention, not only the scales of achromatopsia Type A, B or C can be determined, the scales of achromatopsia Type D, E or F can also be determined.

Also, according to this invention, a camera obscura can be mounted on said displaying means, a pair of oculars are set on the front side of the camera obscura, for the examinee to look into and identify the charts on the displaying means through said oculars; a monitoring ocular is mounted on one side of the camera obscura, for the inspector to look into the charts displayed on the displaying means, to determine if the examinee could make correct chart identification. Thus, the intervention to the diagnostic and correction effects by outside light can be avoided.

Also, according to this invention, a slot can be made on each of the oculars. An achromatopsia correction lens can be fitted into the slots. Besides, a knob is mounted with each of the slots, used for altering the angle of the achromatopsia correction lens, so as to determine the achromatopsia scales of achromatopsia Type D, E or F.

Also, according to this invention, a baffle can be installed in each of the oculars, each baffle is connected to a knob, the baffle is controlled by handling the knob, making it to obstruct the sight of the examinee, or making it to move out from the position where the sight of the examinee is obstructed.

Because the achromatopsia inspection apparatus can precisely diagnose the types and scales of the achromatopsia, it can make correction to a single eye of the achromate. In this case, the single eye without wearing the achromatopsia correction lens can make the brightness of achromatopsia correction same as normal people, to achieve the goal of achromatopsia correction.

BRIEF DESCRIPTION OF THE DRAWINGS

The following is a detailed description of the preferred embodiments of this invention in combination with the attached drawings.

SPECIFIC MODES FOR CARRYING OUT THE INVENTION

Figure 1:
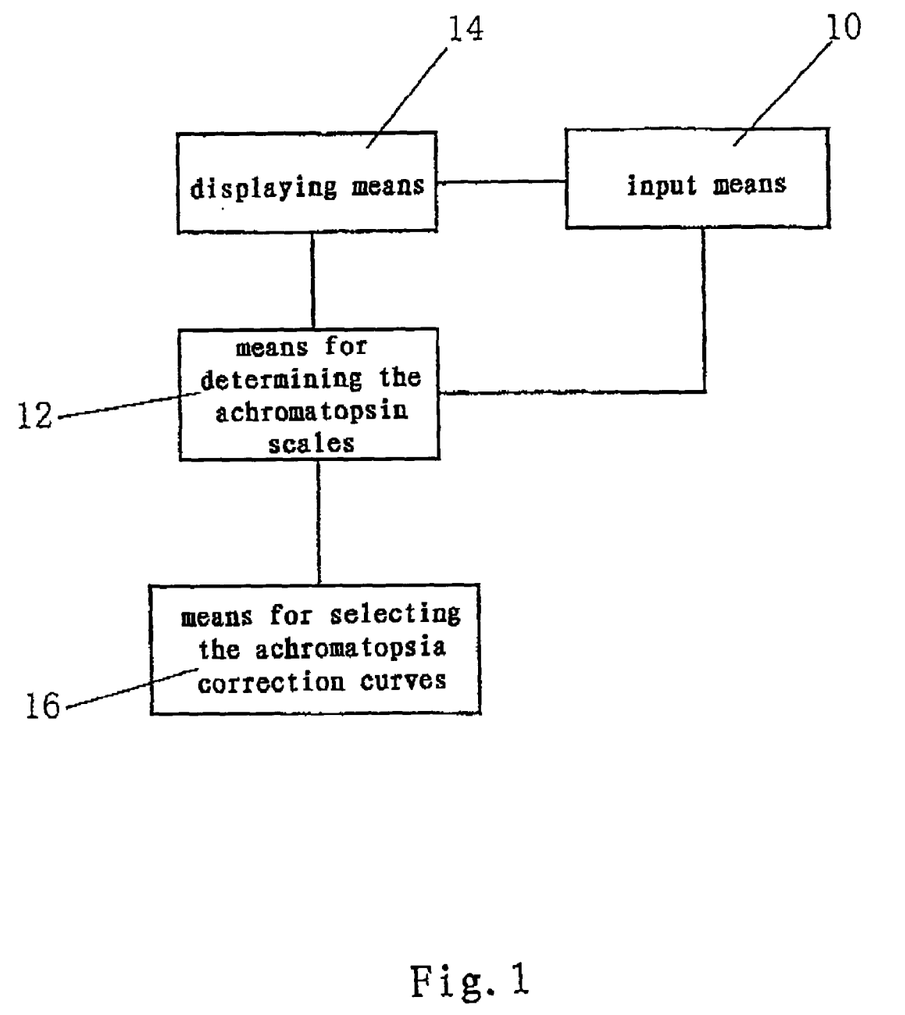
FIG. 1 is a block diagram of the achromatopsia inspection apparatus in this invention.

As shown in FIG. 1, according to this invention, the color vision inspection/correction apparatus comprises: a input means 10, an achromatopsia scale determining means 12, a displaying means 14, and an achromatopsia correction spectrum curve selecting means 16. The input means 10 can be a keyboard, used for the inspector such as a doctor to enter instructions, and for the examinee to enter color-matching results, The displaying means 14 is used for displaying the color vision test chart and colored color-matching contrast charts. The achromatopsia scale determining means 12 determines the scales of the achromatopsia according to the color-matching results entered by the examinee. The achromatopsia correction spectrum curve selecting means 16 selects achromatopsia correction spectrum curves that are suitable for the examinee, according to the achromatopsia type and achromatopsia scales determined by the achromatopsia scale determining means 12. Besides, the color vision inspection/correction apparatus may also include a printer, used for printing achromatopsia correction spectrum curves and diagnostic prescriptions.

During inspection, the displaying means 14 displays a plurality of groups of achromatopsia test charts, each group is corresponding to one type of achromatopsia. FIG. 5 (5A–5F) provides 6 groups of exemplificative color vision test charts, used for respectively inspecting achromatopsia Type A–F; if the examinee is unable to identify the patterns, numerals or letters in FIG. 5A, he/she is a Type A achromate, if the examinee is unable to identify the patterns, numerals or letters in FIG. 5B, he/she is a Type B achromate, and on the analogy of this. If all of them are identified, the examinee has a normal color vision; if all of them are not identified, the examinee is a complete achromate. The background colors and the colors of patterns, numerals or letters in the 24 color vision test charts provided by FIGS. 5A–5F are unchangeable, but the patterns, numerals or letters change randomly, in order to avoid recitation.

In order to automatically deliver the inspection results on the achromatopsia types, the achromatopsia scale determining means 12 may also store a comparison table, from which the correct patterns, numerals or letters contained in each of the color vision test charts can be searched out. The achromatopsia scale determining means 12 determines the types of achromatopsia according to the identification results entered through the input means 10 by searching said comparison table.

Figure 6A:
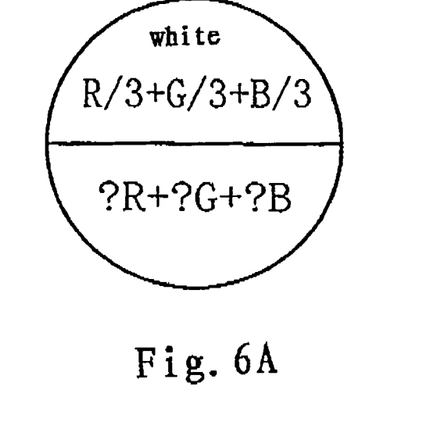
FIGS. 6A–6D are the colored color-matching contrast charts for the color vision inspection apparatus for determining the scales of achromatopsia Type A, B or C.
Figure 6B:
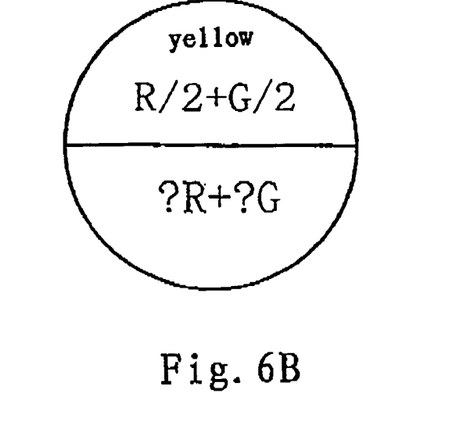
Figure 6C:
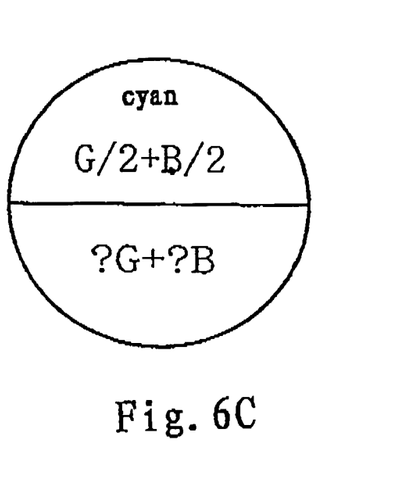
Figure 6D:
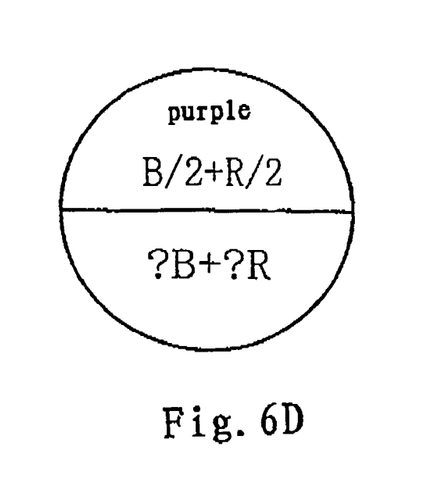

In order to diagnose the scales of achromatopsia Type A, B and C, the displaying means 14 can also display at least one colored color-matching contrast charts. FIGS. 6A–6D gives an example of such a colored color-matching contrast charts. In FIG. 6A, the upper half of the circular is in white color, which is composed of 1/3R+1/3G+1/3B, the under half of the circular is for the examinee to match color. The examinee makes up white color same as the upper half by adjusting the values of R, G and B through the input means. Then the achromatopsia scale determining means 12 distinguishes the achromatopsia scales according to the predetermined differences on the three elementary colors with normal people. The three elementary colors on the displaying means 14 are marked off into 63 scales, the color brightness is marked off into 10 grades, so as to make them compliant with human's color vision. Obviously, normal people can make up white color same as the upper half of the circular using 21/63R+21/63G+21/63B, but Type A achromate may use 27/63R, 30/63R, 33/63R, 36/63R, 39/63R or 42/63R to make up white color "same" as the upper half of the circular, Type B achromate may use 27/63G, 30/63G, 33/63G, 36/63G, 39/63G or 42/63G to make up white color "same" as the upper half of the circular, and on the analogy of this. The make-up results falling into the circumstances of (27±1)/63, (30±1)/63, (33±1)/63, (36±1)/63, (39±1)/63 or (43±1)/63, they are defined into 6 different scales, and are indicated respectively by $A_{1-6}$, $B_{1-6}$, and $C_{1-6}$. In FIGS. 6B–6D, the upper half of the circulars are respectively yellow made up of 1/2R+1/2G, cyan made up of 1/2G+1/2B and purple made up of 1/2B+1/2R, the under halves of the circulars are still for the examinee to makeup colors same as the upper halves of the circulars by adjusting the two elementary colors through the input means. The accuracy of the inspection can be enhanced by taking the average value of the above four make-up results.

Figure 2A:
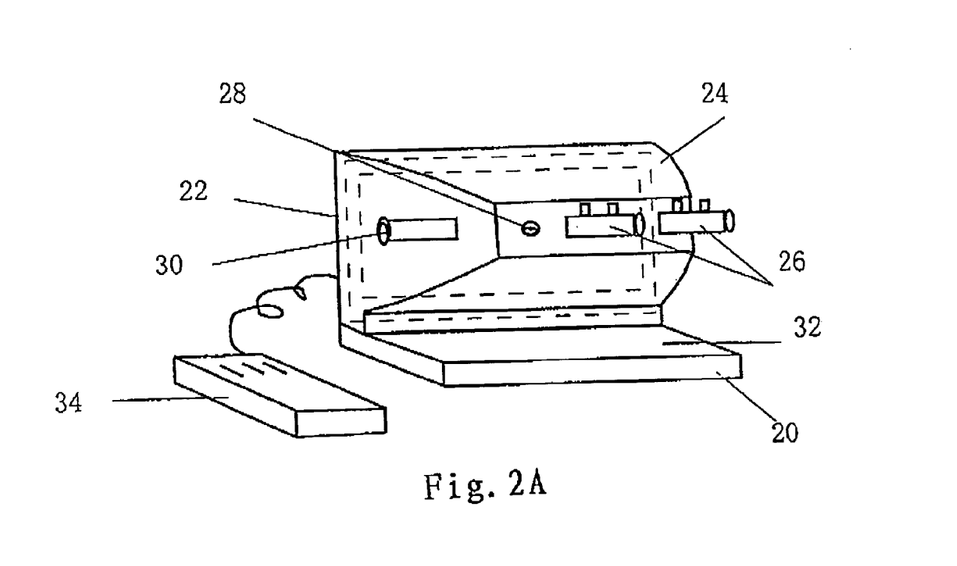
FIGS. 2A, 2B and 2C are respectively the solid view, left side view and whole view of the color vision inspection apparatus in the preferred embodiments of this invention.
Figure 2B:
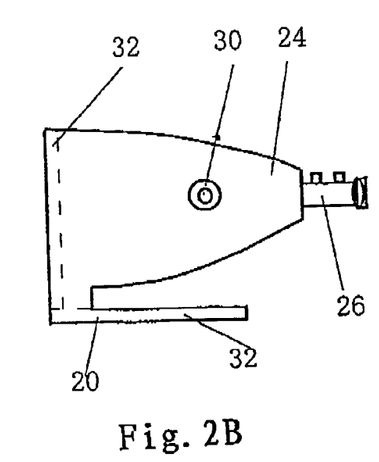
Figure 2C:
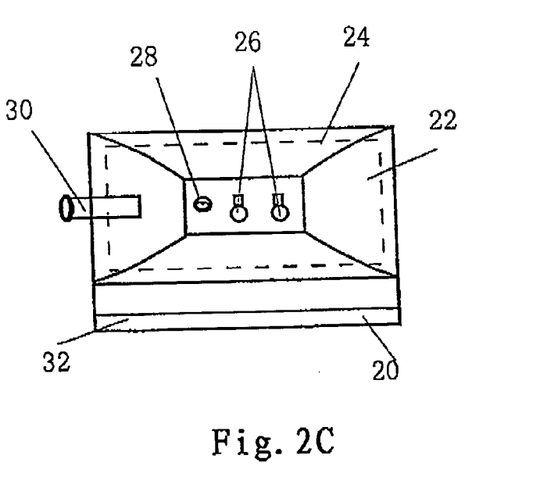

FIGS. 2A–2C shows a preferred embodiment of the achromatopsia inspection/correction apparatus in this invention. As shown in these figures, the achromatopsia inspection/correction apparatus includes a laptop computer having a main-body 20, a colored display 22 and a keyboard 32. It is obvious that this invention can be realized with other kind of computers. A camera obscura 24 is mounted on the display 22, two monoculars 26 are mounted on the camera obscura Acing the display 22, their intervals can be adjusted through the knob 28, so as to be used by examinee with different space between pupils. A monitoring ocular 30 is mounted on the side of the camera obscura 24, for the inspector to monitor the display and give instructions to the examinee. The inspection results can be printed by printer 34.

Figure 3:
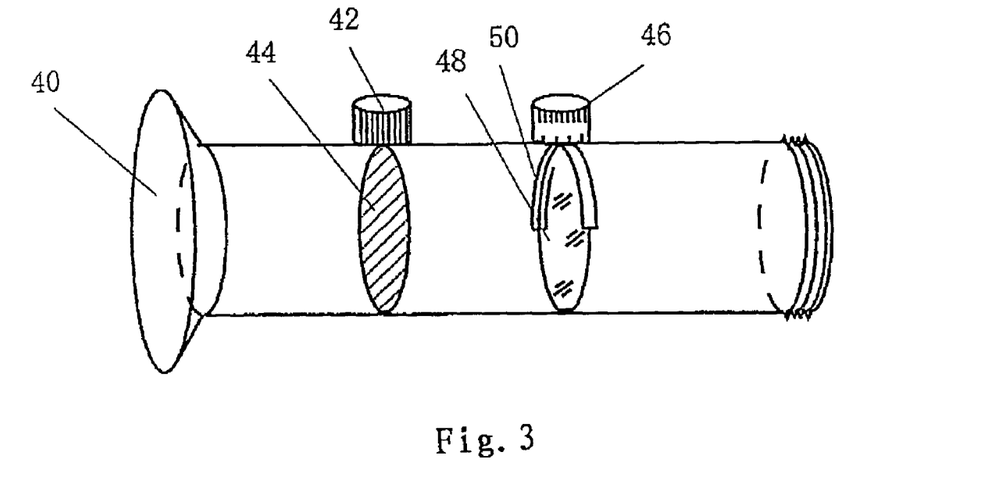
FIG. 3 is a structural schematic illustration of a watching ocular of the color vision inspection apparatus.

As shown in FIG. 3, there are slots on the oculars 26, where the achromatopsia correction lens 48 can be plugged in. The achromatopsia correction lens 48 is fixed into the lens frame 50, which is connected to the achromatopsia correction knob 46. The achromatopsia correction knob 46 has a graduation indicating the wavelength. The rotating angle of the correction knob 46 (such as 0–45°) is corresponding to the wavelength (such as 0–30 nm). Besides, a baffle 44 is set within the oculars 26, and is connected to a baffle knob 42. The baffle 44 can be opened or closed by rotating the baffle knob 42. The oculars 26 can be used as a monocular or used as binoculars. The examinee can identify the color vision test chart on the display 22 or conduct color-matching to the color matching contrast charts through the watching window 40.

Figure 4:
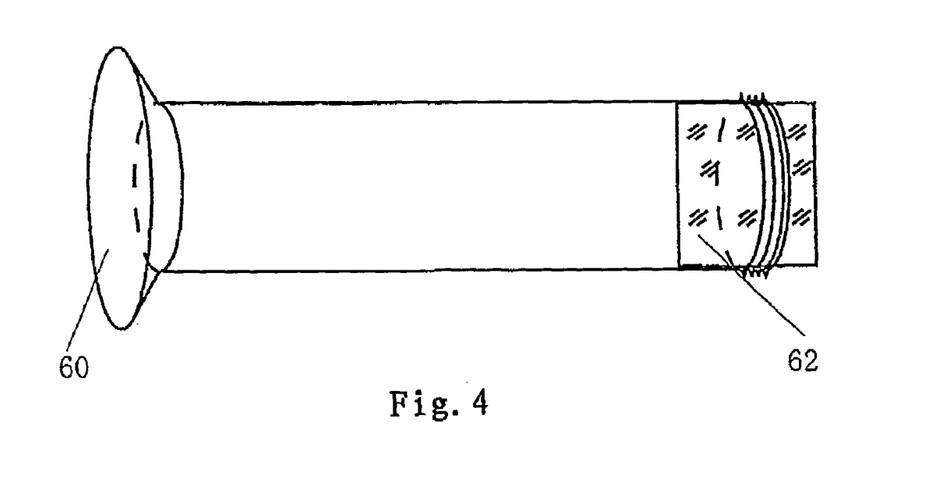
FIG. 4 is a structural schematic illustration of the monitoring ocular of the color vision inspection apparatus.
Figure 5A:
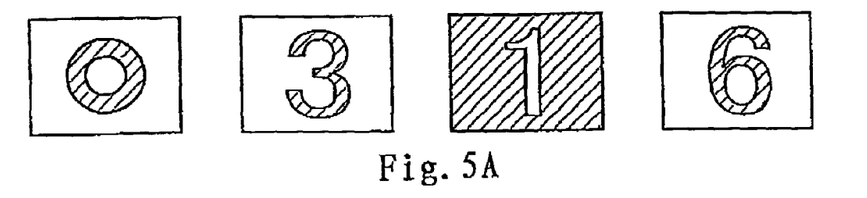
FIGS. 5A–5F are the color vision test charts for the color vision inspection apparatus according to the preferred embodiments of this invention, for the inspection of achromatopsia Type A to F.
Figure 5B:
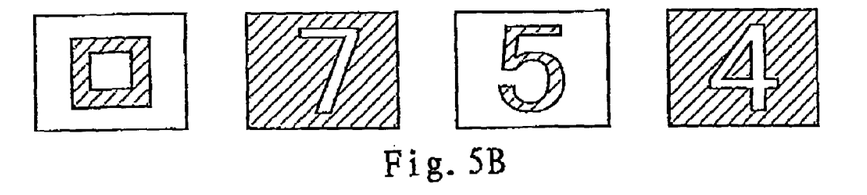
Figure 5C:
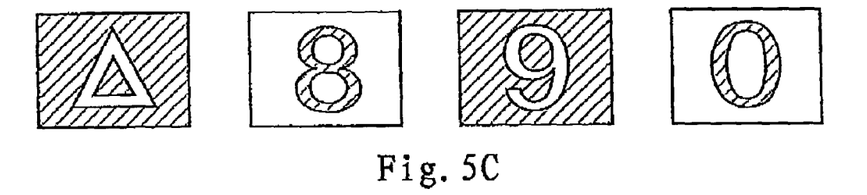
Figure 5D:
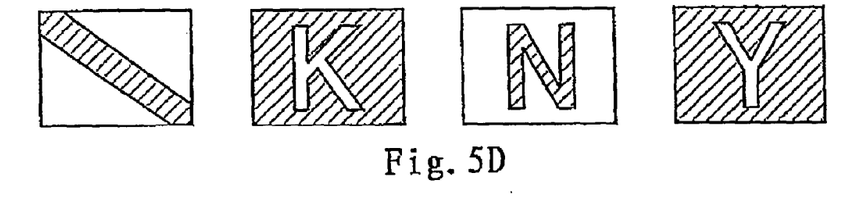
Figure 5E:
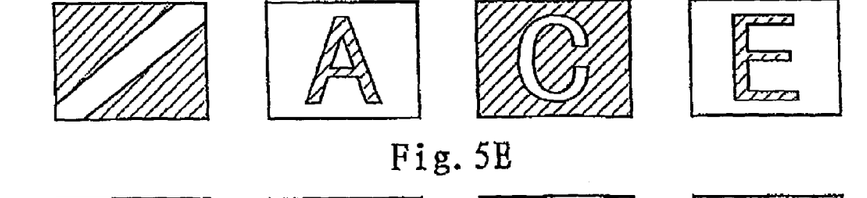
Figure 5F:
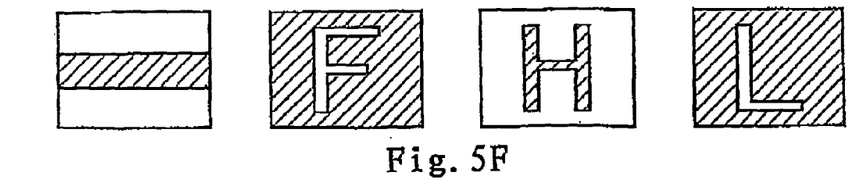

As shown in FIG. 4, a monitoring ocular 30 has a prism 62 deep inside the camera obscura 24. Through the monitoring window 60, the inspector can see clearly the changes of patterns on the display 22, so as to give instructions to the examinee on the handling method.

Figure 7A:
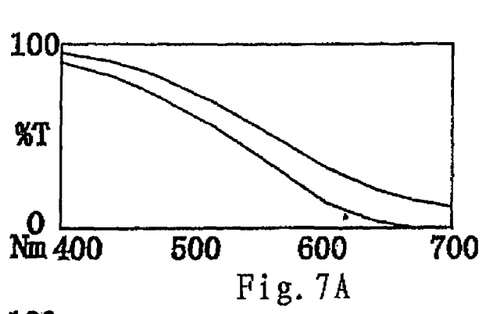
FIGS. 7A–7F are the achromatopsia correction spectrum curves of this invention, corresponding to achromatopsia Type A to F.
Figure 7B:
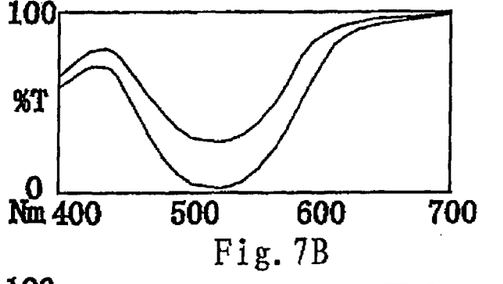
Figure 7C:
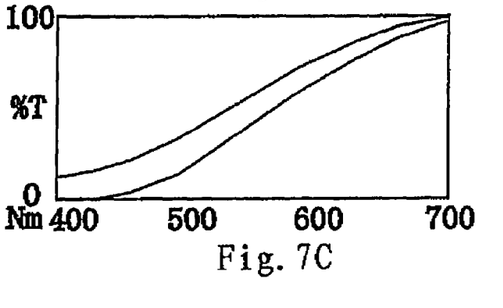
Figure 7D:
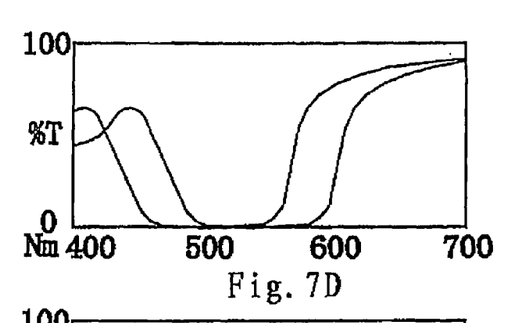
Figure 7E:
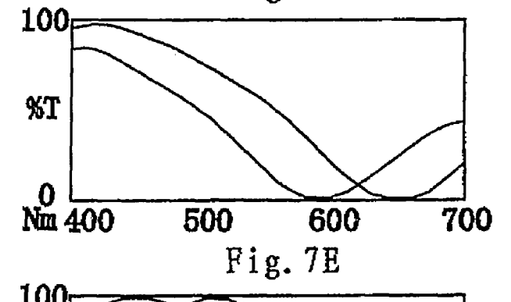
Figure 7F:
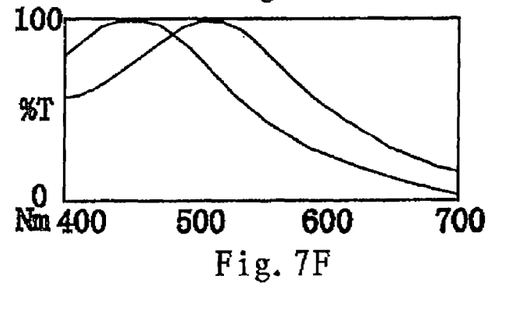

The scales of achromatopsia Type D, E or F are determined according to the shifting volume of the wavelength corresponding to the rotation angle of achromatopsia correction lens 48, as shown in the achromatopsia spectrum curves in FIGS. 7D, 7E or 7F, that are plugged into the watching oculars 26. It is prescribed that every 10 nm shifting of the maximum spectrum absorbing wavelength of one of the three elementary colors is a scale, indicated respectively by $D_{1-6}$, $E_{1-6}$ and $F_{1-6}$.

After the types and scales of achromatopsia are diagnosed by the color vision inspection apparatus, the achromatopsia correction lenses corresponding to the diagnosed types and scales of achromatopsia (such as $A_5$, $B_4$, $E_1$) can be plugged into the achromatopsia correction lens-frame 50, and then having the examinee to look at all the test charts as in FIGS. 5A–5F, and match colors on the color-matching contrast charts as in FIGS. 6A–6D. After passing all tests, the inspection finishes, ran the printer and print medical certificate and correction prescription.

There are 6 kinds of correction lenses for each of the achromatopsia type, respectively corresponding to 6 scales. FIGS. 7A–7F have provided the achromatopsia correction spectrum curves respectively corresponding to the achromatopsia correction lenses for achromatopsia Types A to F. There should be 6 achromatopsia correction spectrum curves for each type, only 2 curves are provided here for simplicity.

For achromatopsia type A, B or C, the correction curves should meet the following equation:

$$F(\lambda) = Ae^{-\left(\frac{\lambda-600}{\alpha}\right)^2} + Be^{-\left(\frac{\lambda-535}{\beta}\right)^2} + Ce^{-\left(\frac{\lambda-440}{\gamma}\right)^2},$$

Wherein the value of A, B or C is 1/63, 2/63/, 3/63/, . . . , 63/63, and A+B+C=1, λ is wavelength, α, β, γ are weighting indexes.

For achromatopsia type D, E or F, the correction curves should meet the following equation:

$$F(\lambda) = Ae^{-\left(\frac{\lambda+\lambda_D-600}{\alpha}\right)^2} + Be^{-\left(\frac{\lambda+\lambda_E-535}{\beta}\right)^2} + Ce^{-\left(\frac{\lambda+\lambda_F-440}{\gamma}\right)^2},$$

Wherein the value of A, B or C is 1/63, 2/63/, 3/63/, . . . , 63/63, and A+B+C=1, λ is wavelength, α, β, γ are weighting indexes, and $\lambda_D$, $\lambda_E$, $\lambda_F$ are shifting values of the wavelength.

Figure 8:
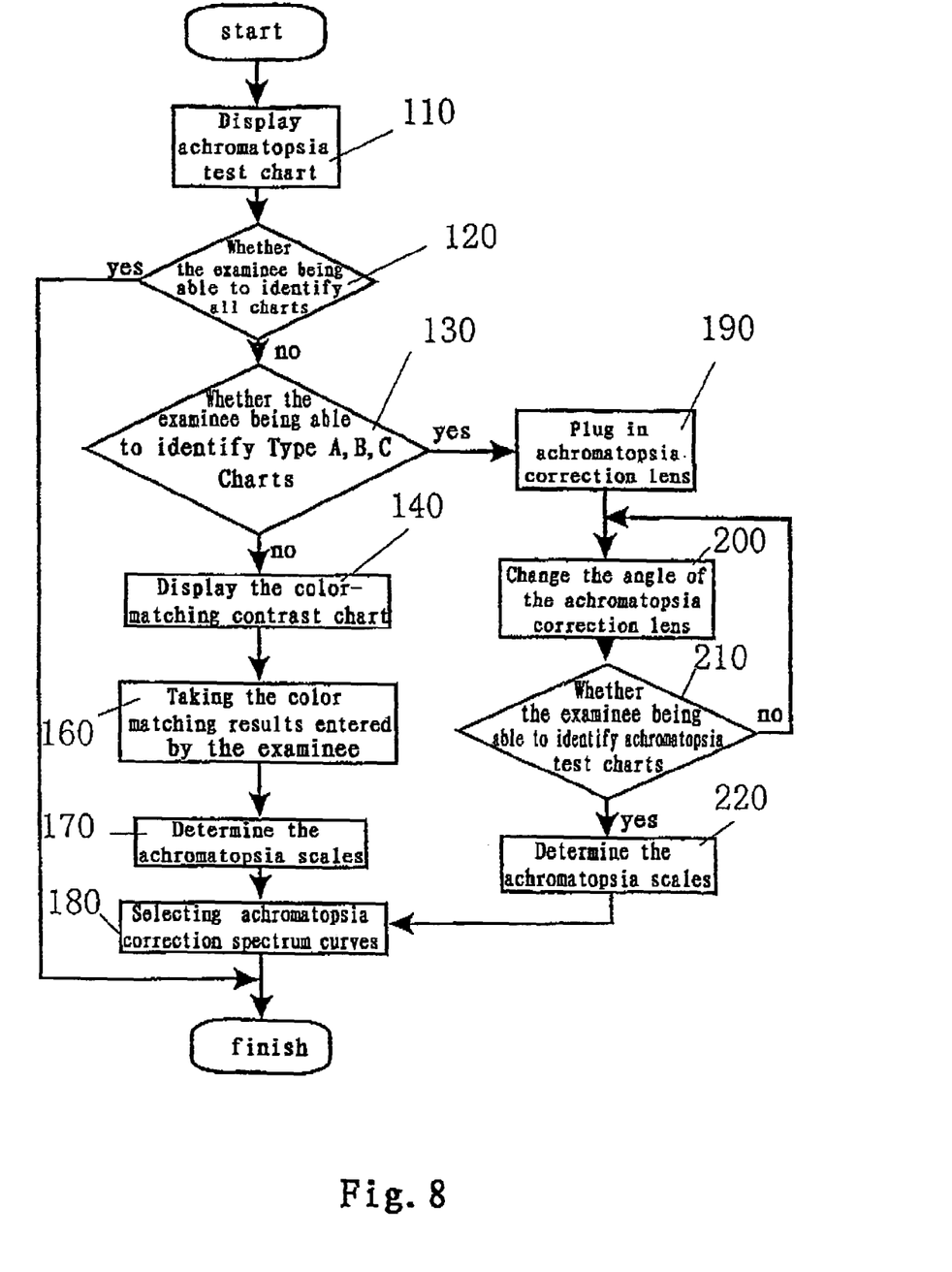
FIG. 8 is a flow chart of the color vision inspection/correction method.

The following is a detailed description of the achromatopsia inspection/correction method of this invention with reference to FIG. 8.

As shown in FIG. 8, when starting the achromatopsia inspection, in step 110, each group of the achromatopsia test charts as shown in FIGS. 5A–5F are displayed ordinally on the displaying means 14 for the examinee to identify. In step 120, if the examinee can correctly identify all the groups of achromatopsia test charts, which means the examinee has a normal color vision, the inspection process would be over. If he/she cannot identify all of them, the following step 130 is used to determine the achromatopsia types. If it belongs to Types A, B or C, then the colored color-matching contrast charts as shown in FIGS. 6A–6D are displayed on the displaying means 14 (step 140). The examinee conducts color-matching through input means 10, the color-matching results are taken by achromatopsia scale determining means 12 (step 160). In step 170, the achromatopsia scale determining means 12 determines the types and scales of achromatopsia according to the color-matching results, in the previously described manner. And then, in step 180, the achromatopsia correction spectrum curve selecting means 16 selects corresponding achromatopsia correction spectrum curves according to the determined achromatopsia types and scales.

If step 130 determines the achromatopsia type to be Types D, E or F, the achromatopsia correction lenses corresponding to achromatopsia Types D, E or F can be plugged into the achromatopsia correction lens frame 50 (step 190). Then, altering the angle of the lenses and ask the examinee to identify, until the examinee can distinguish correctly all the achromatopsia test charts (step 200, 210). After that, in step 220, determining the achromatopsia scales according to the magnitude of the rotation angle of the achromatopsia correction lens, and selecting the corresponding achromatopsia correction spectrum curves according to the determined achromatopsia types and scales (step 180).

The examinee is asked to put on the achromatopsia correction lens selected according to the determined achromatopsia correction spectrum curves, and he/she is asked to identify the achromatopsia test charts as shown in FIGS. 5A–5F, if all of them are correctly identified, the final inspection is passed. Otherwise, determining the achromatopsia scales again in the above method, until the examinee can correctly identify all the achromatopsia test charts.

In summary, by using the color vision inspection apparatus of this invention, the achromatopsia types and scales can be accurately diagnosed, this makes possible the single eye correction based on the accurate diagnostic results. For the theory of achromatopsia correction by single eye wearing achromatopsia correction lens, please consult "*Introduction on the Correction of Color Vision*", by Chen Xiaoguang, published by Jilin Technology Publishing Company, 1992.

The above is a detailed description to this invention, in combination with the preferred embodiments. There needs to be pointed out, various kinds of changes can be made to the specific embodiments under the teaching of this invention. These changes should be considered as within the scope of this invention.

What is claimed is:

1. An achromatopsia inspection/correction method, comprising the following steps:

displaying on a displaying means a plurality of groups of achromatopsia test charts for the examinee to identify, each group being corresponding to one type of achromatopsia;

determining the types of achromatopsia based upon the identifying results;

displaying at least one colored color-matching contrast chart, one area of said color-matching chart being in a predetermined color, another area being for the examinee to match colors;

taking the color-matching result from the examinee;

determining the achromatopsia scales of the examinee by comparing the color-matching results of the examinee with the three elementary colors of said predetermined color, wherein each of the three elementary colors on the displaying means being divided into 63 scales;

selecting a corresponding achromatopsia correction spectrum curves according to the determined types and scales of achromatopsia.

2. The achromatopsia inspection/correction method according to claim 1, characterized in that, when the examinee is determined to be achromatopsia Type D, E or F the process of determining the types of achromatopsia further comprises the following steps:

providing an achromatopsia correction lens;

making the examinee identify achromatopsia test charts through said achromatopsia correction lens;

altering the angle of said achromatopsia correction lens until the examinee is able to correctly identify said achromatopsia test charts;

determining the achromatopsia scales according to said angle.

3. The achromatopsia inspection/correction method according to claim 1, characterized in that, when the achromatopsia type is Type A, B or C, the selected achromatopsia correction spectrum curves meet the equation:

$$F(\lambda) = Ae^{-\left(\frac{\lambda-600}{\alpha}\right)^2} + Be^{-\left(\frac{\lambda-535}{\beta}\right)^2} + Ce^{-\left(\frac{\lambda-440}{\gamma}\right)^2},$$

wherein each of A, B and C has value of any one selected from 1/63, 2/63/, 3/63, . . . , 63/63, and A+B+C=1, $\lambda$ is wavelength, and $\alpha$, $\beta$,$\gamma$ are weighting indexes.

4. The achromatopsia inspection/correction method according to claim 2, characterized in that, when the achromatopsia type is Type D, E or F, the selected achromatopsia correction spectrum curves meets the equation:

$$F(\lambda) = Ae^{-\left(\frac{\lambda+\lambda_D-600}{\alpha}\right)^2} + Be^{-\left(\frac{\lambda+\lambda_E-535}{\beta}\right)^2} + Ce^{-\left(\frac{\lambda+\lambda_F-440}{\gamma}\right)^2},$$

wherein each of A, B and C has value of any one selected from 1/63, 2/63/, 3/63, . . ., 63/63, and A+B+C=1, $\lambda$ is wavelength, $\alpha,\beta,\gamma$ are weighting indexes, and $\lambda_D,\lambda_E,\lambda_F$ are shifting values of the wavelength.

5. An achromatopsia inspection/correction apparatus comprising:

a displaying means, for displaying a plurality of groups of achromatopsia test charts, each group corresponding to one type of achromatopsia, for the examinee to identify; and for displaying at least one colored color-matching contrast charts, with one area of the color-matching chart being in a predetermined color and another area being used for the examinee to match colors;

an input means, for taking a color-matching result from the examinee;

a means for determining an achromatopsia scales of the examinee by comparing the color-matching results from the examinee with three elementary colors of said predetermined color, wherein each of the three elementary colors on the displaying means being divided into 63 scales;

a means for selecting a corresponding achromatopsia correction spectrum curves according to the identified type and determined scale of achromatopsia.

6. The achromatopsia inspection/correction apparatus according to claim 5, characterized in that, said achromatopsia scale determining means includes a comparison table, from which correct patterns, numerals or letters contained in each of the achromatopsia test charts can be searched out, whereby the achromatopsia scale being determined automatically by comparing the correct patterns, numerals or letters contained in said achromatopsia test charts with the results entered by the examinee through the input means.

7. The achromatopsia inspection/correction apparatus according to claim 5, further comprising a printer, used for printing the selected achromatopsia correction spectrum curves.

8. The achromatopsia inspection/correction apparatus according to claim 5, characterized in that a camera obscura being mounted on the displaying means, two monoculars being set on the front side of the camera obscura, for the examinee to look into and identify the charts on the displaying means through said two monoculars, a mounting ocular being mounted on one side of the camera obscura, for an inspector to look into the charts displayed on the displaying means, to determine whether or not the examinee makes correct chart identification.

9. The achromatopsia inspection/correction apparatus according to claim 8, characterized in that, a space between the two monoculars can be adjusted.

10. The achromatopsia inspection/correction apparatus according to claim 8, characterized in that the monitoring ocular has a prism plugged inside the camera obscura.

11. The achromatopsia inspection/correction apparatus according to claim 8, characterized in that each of the oculars has a slot into which an achromatopsia correction lens can be plugged.

12. The achromatopsia inspection/correction apparatus according to claim 11, characterized in that a knob is mounted for each of the slots, used for altering an angle of the achromatopsia correction lens, so as to determine the achromatopsia scales of achromatopsia of Type D, B or F according to a rotation angle of the knob.

13. The achromatopsia inspection/correction apparatus according to claim 11, characterized in that a baffle is installed in each of the two monoculars, each baffle being connected to a knob, the baffle being controlled by handling the knob, so as to obstruct the sight of the examinee, or move out from a position where the sight of the examinee is obstructed.

14. The achromatopsia inspection/correction apparatus according to claim 5, characterized in that a background and colors of patterns, numerals or letters in the achromatopsia test charts are unchangeable, but patterns, numerals or letters change randomly.

15. The achromatopsia inspection/correction apparatus according to claim 5, characterized in that a color brightness is divided into 10 grades.

16. The achromatopsia inspection/correction apparatus according to claim 5, characterized in that, when the achromatopsia type is Type A, B or C, the selected achromatopsia correction spectrum curves the equation:

$$F(\lambda) = Ae^{-\left(\frac{\lambda-600}{\alpha}\right)^2} + Be^{-\left(\frac{\lambda-535}{\beta}\right)^2} + Ce^{-\left(\frac{\lambda-440}{\gamma}\right)^2},$$

wherein each of A, B and C has value of any one selected from 1/63, 2/63, 3/63, . . ., 63/63, and A+B+C=1, $\lambda$ is wavelength, and $\alpha,\beta,\gamma$ are weighting indexes.

17. The achromatopsia inspection/correction apparatus according to claim 5, characterized in that, when the achromatopsia type is Type D, E or F, the selected achromatopsia correction spectrum curves the equation:

$$F(\lambda) = Ae^{-\left(\frac{\lambda+\lambda_D-600}{\alpha}\right)^2} + Be^{-\left(\frac{\lambda+\lambda_E-535}{\beta}\right)^2} + Ce^{-\left(\frac{\lambda+\lambda_F-440}{\gamma}\right)^2},$$

wherein each of A, B and C has value of any one selected from 1/63, 2/63, 3/63, . . ., 63/63, and A+B+C==1, $\lambda$ is wavelength, $\alpha,\beta,\gamma$ are weighting indexes, and $\lambda_D, \lambda_E, \lambda_F$ are shifting values of the wavelength.

18. The achromatopsia inspection/correction method according to claim 1, characterized in that, correction can be made to a single eye based upon the types and scales of achromatopsia checked out by said achromatopsia inspection method.

19. The achromatopsia inspection/correction apparatus according to claim 5, characterized in that, correction can be made to a single eye based upon the type and scale of achromatopsia checked out by said achromatopsia inspection apparatus.

* * * * *